United States Patent [19]
Eason et al.

[11] Patent Number: 5,769,073
[45] Date of Patent: Jun. 23, 1998

[54] POWDER INHALATOR

[75] Inventors: Stephen William Eason, Redgrave; Clive Patrick Catterall, Wantage; Roger William Clarke, Histon; Donna Joy Wilson, Cambridge, all of Great Britain

[73] Assignee: Merck Patent Gesellschaft mit Beschrankter Haftung, Germany

[21] Appl. No.: 663,245

[22] PCT Filed: Dec. 9, 1994

[86] PCT No.: PCT/GB94/02716

§ 371 Date: Aug. 29, 1996

§ 102(e) Date: Aug. 29, 1996

[87] PCT Pub. No.: WO95/16483

PCT Pub. Date: Jun. 22, 1995

[30] Foreign Application Priority Data

Dec. 18, 1993 [GB] United Kingdom .................. 9325835
May 17, 1994 [GB] United Kingdom .................. 9409841

[51] Int. Cl.[6] .......................... A61M 11/00; A61M 15/00; A61M 16/00
[52] U.S. Cl. ................................. 128/203.15; 128/200.21; 128/200.22; 128/200.23; 128/200.24; 128/203.12; 128/203.21
[58] Field of Search .......................... 128/200.21, 200.22, 128/200.23, 200.24, 200.25, 203.12, 203.15, 203.21; 222/742.6

[56] References Cited

U.S. PATENT DOCUMENTS

| 5,337,740 | 8/1994 | Armstrong et al. | 128/203.12 |
| 5,388,572 | 2/1995 | Mulhauser et al. | 128/203.15 |
| 5,492,112 | 2/1996 | Meikalski et al. | 128/203.15 |

FOREIGN PATENT DOCUMENTS

| 0407028 | 1/1991 | European Pat. Off. . |
| 0547429 | 6/1993 | European Pat. Off. . |
| 91/06333 | 5/1991 | WIPO . |
| 92/00771 | 1/1992 | WIPO . |
| 93/24166 | 12/1993 | WIPO . |

*Primary Examiner*—V. Millin
*Assistant Examiner*—Dinh X. Nguyen
*Attorney, Agent, or Firm*—Millen, White, Zelano & Branigan, P.C.

[57] ABSTRACT

A device for dispensing doses of powdered material comprises a housing which houses a cylindrical container. The container has a number of helically arranged compartments each of which contains a respective dose of powdered material. In order to dispense the material from a compartment, that compartment is moved into registry with an airway in the device by means of an indexing mechanism, and the user sucks on a mouthpiece of the housing, which mouthpiece communicates with an air inlet via the airway. The flow of air through the airway ejects the dose of material. The container can constitute a replaceable cartridge. The device is particularly suitable for use as an inhaler for dispensing powdered medicament.

16 Claims, 12 Drawing Sheets

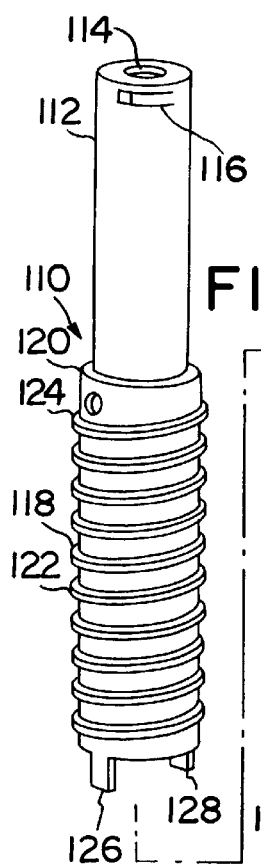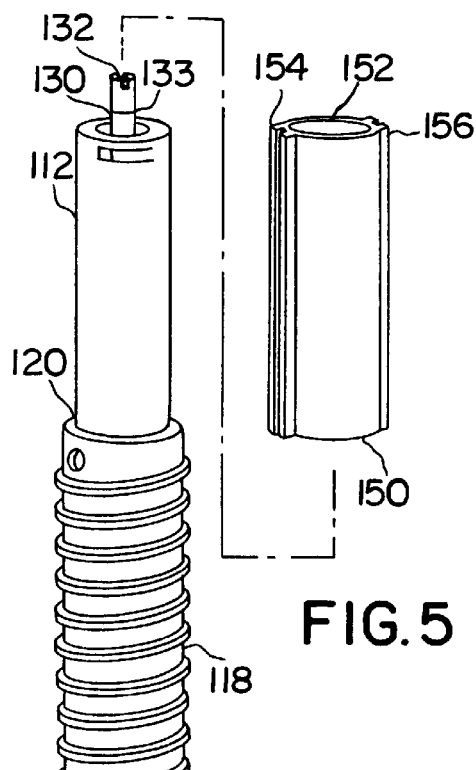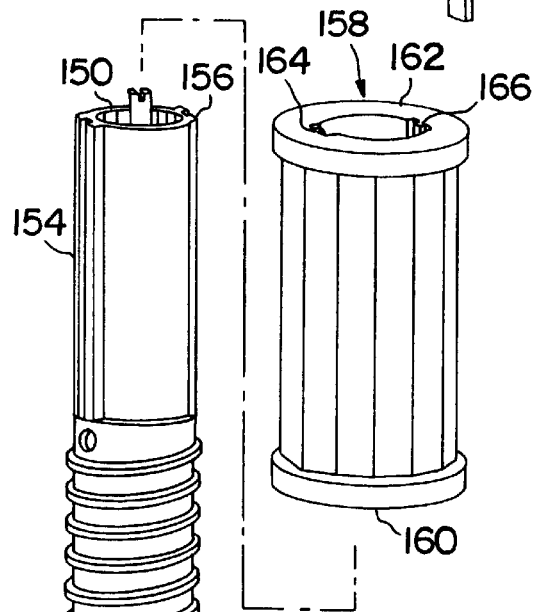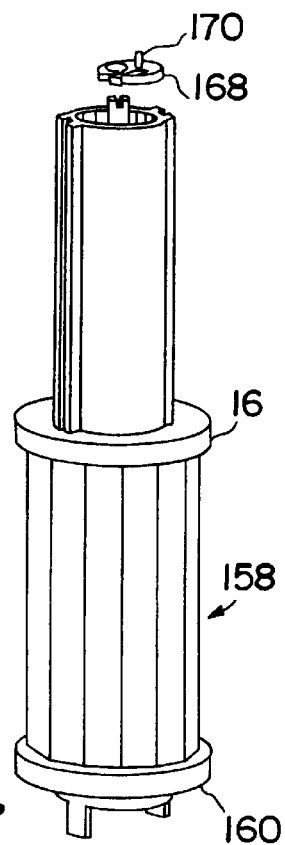

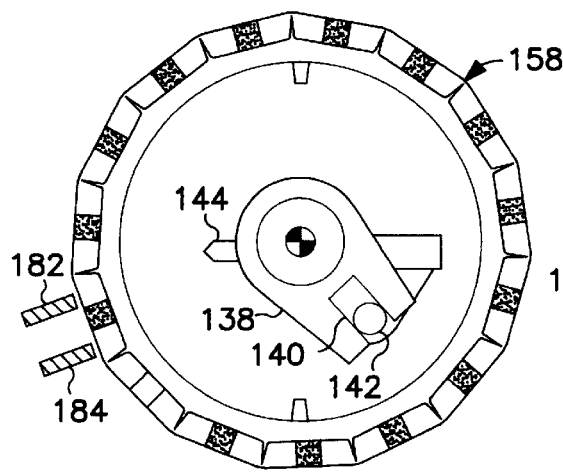 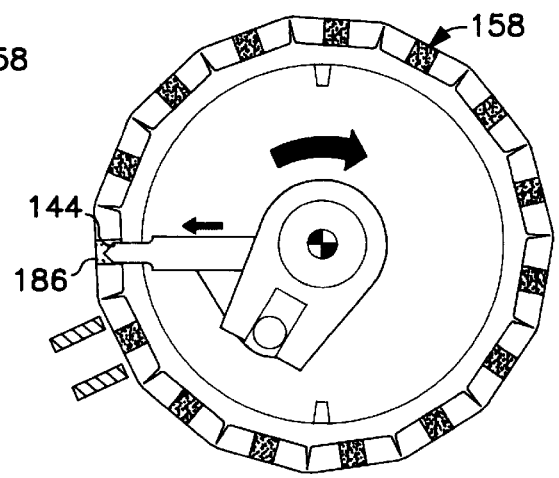
FIG. 11A    FIG. 11B
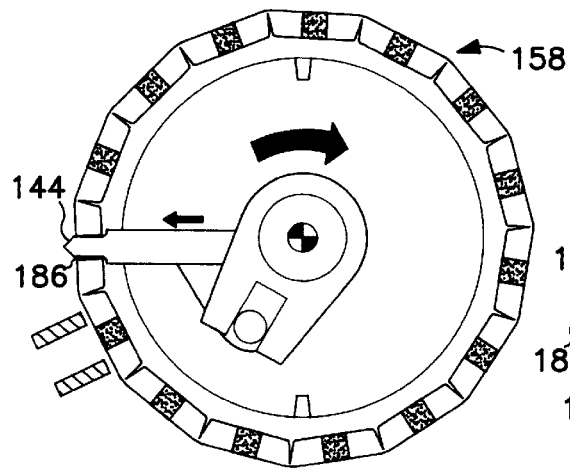 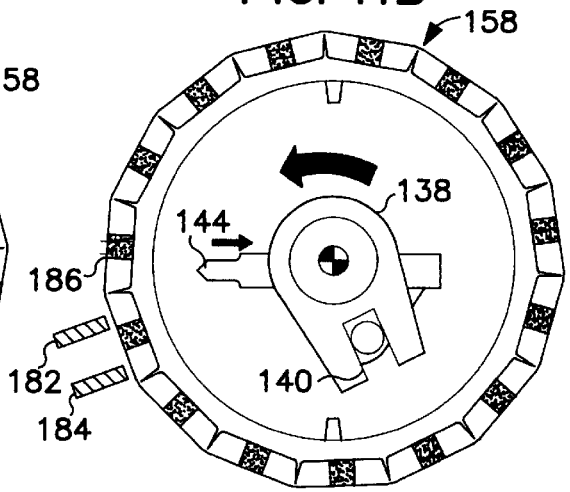
FIG. 11C    FIG. 11D
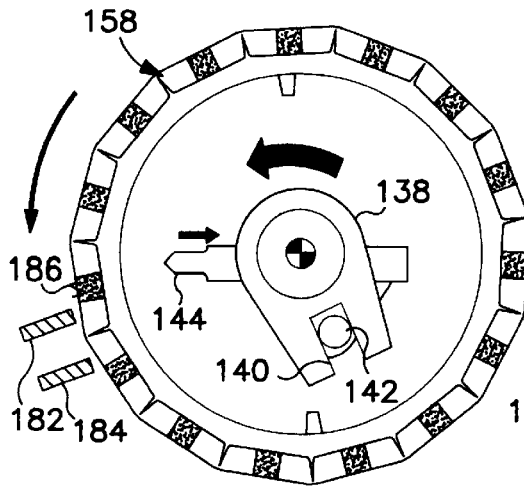 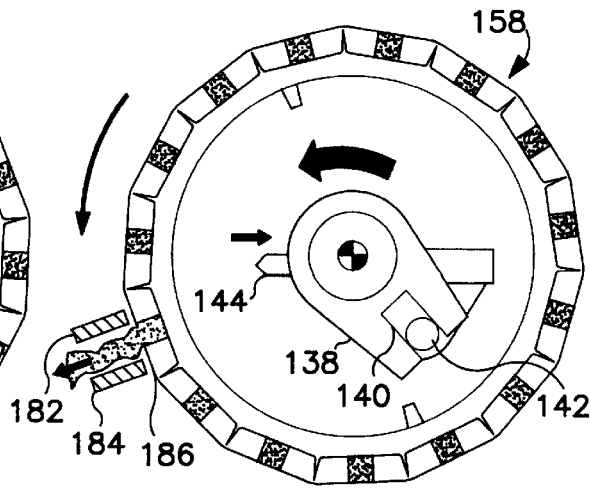
FIG. 11E    FIG. 11F

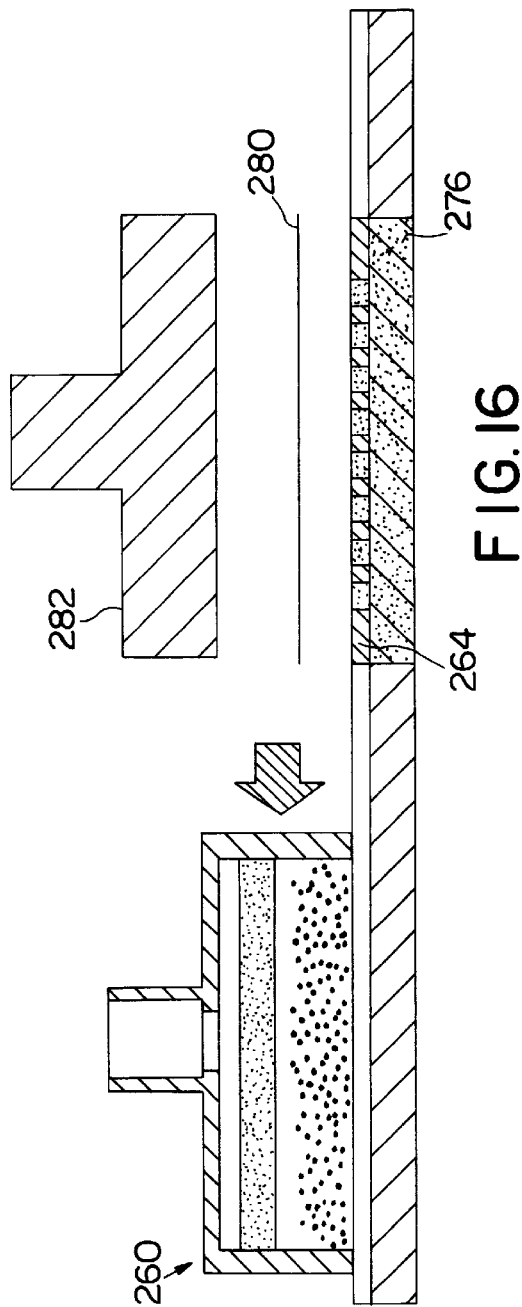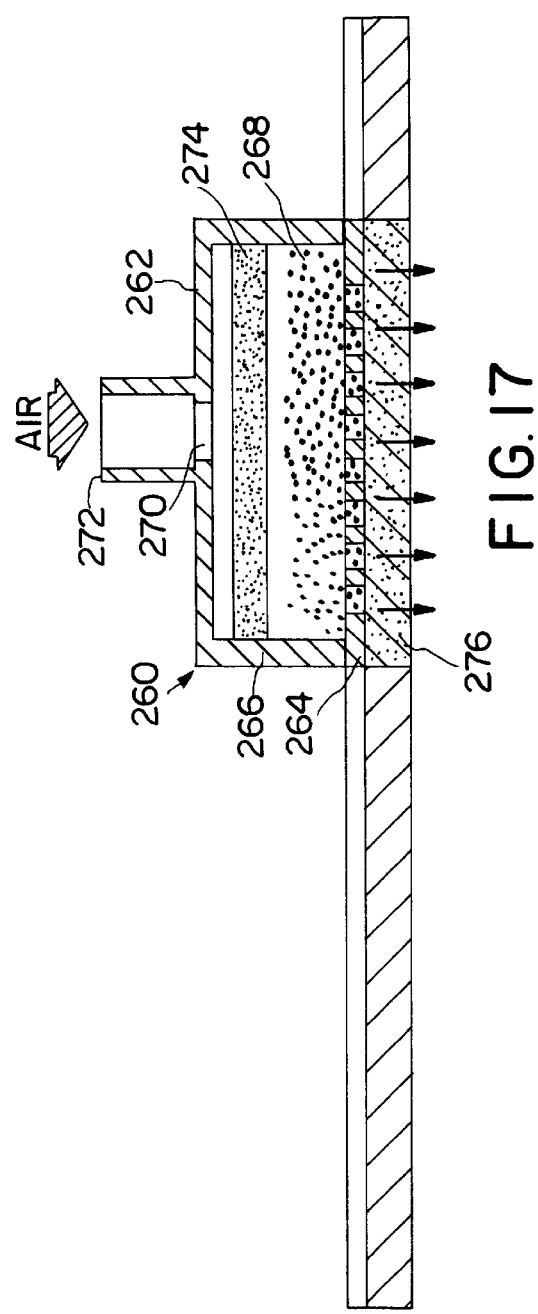

# POWDER INHALATOR

FIELD OF THE INVENTION

This invention concerns devices for administering single doses of particulate material, particularly a medicament in granular or in finely divided powder form and particularly for inhalation to relieve respiratory difficulties. The invention is also concerned with the packaging of single doses of a medicament particularly in powdered form for self administration as by inhalation.

BACKGROUND TO THE INVENTION

It is known to provide a pharmacologically active compound in finely divided particulate form for self administration by inhalation to relieve respiratory problems particularly asthma. One approach for dispensing such material has been to provide a reservoir of finely divided particulate material and to dispense the powdered material in equal predetermined volumes, each predetermined volume corresponding to the dose required by a patient to relieve the asthmatic symptoms during an asthma attack. A device for dispensing such powdered material is described in published UK Patent Specification No. 2144997A.

Pharmacologically active compounds suitable for the treatment of asthma tend to be hygroscopic and this can cause particle agglomeration in a reservoir such as described in UK 2144997.

SUMMARY OF THE INVENTION

According to a first aspect of the invention, there is provided a device for dispensing single doses of a particulate material, the device comprising a housing carrying a mouthpiece which communicates with an air inlet through an airway within the housing, a cylindrical container contained within the housing, the container having a plurality of compartments, each containing a respective dose of particulate material, operating means for moving the container relative to the airway so as to bring successive compartments into registry with the airway, to enable the doses of medicament to be discharged therefrom.

Preferably part of the airway extends along an axial passage within the container, preferably along at least part of the elongate axis of the container.

Preferably, the compartments are angularly and axially spaced relative to each other so as to define a helical path which is substantially coaxial with the axis of the container.

Preferably, the container comprises a tubular body having a plurality of radial bores, each of which constitutes a respective compartment.

According to another aspect of the present invention, there is provided a device for dispensing single doses of a powdered medicament comprising a housing carrying a mouthpiece and having an air inlet, inner and outer relatively rotatable coaxial tubes within the housing, a helically extending platform between the tubes defining a helically extending space, said space being partitioned to define pockets lying on a helical path and each containing a discrete dose of powdered medicament, apertures for passage of air in the walls of the inner and outer tubes, and operating means for relatively rotating the inner and outer tubes, the arrangement being such that said relative rotation brings successive dose-containing pockets into registry with the air apertures in the tubes in the path of an airway extending from the air inlet to the mouthpiece.

Thus, when the user requires medication, it is only necessary to actuate the operating means and then suck on the mouthpiece in order to draw a prescribed dose of medicament into the mouth. The rush of air generated by the sucking action ensures that the pocket is cleaned of medicament, which becomes dispersed in the air drawn into the mouth. The helical arrangement of pockets enables a large number of doses of medicament to be contained in a relatively compact device.

Each dose of powdered medicament may be sufficiently tightly packed in its respective pocket to be self supporting, therein.

Alternatively, the powdered doses may be relatively loosely packed in the corresponding pockets in which case the device preferably includes sealing means for retaining the doses of material in the corresponding pockets.

The sealing means could comprise one or more membranes (of for example, foil) covering the pockets, the device including means for rupturing each membrane to allow the powdered material to be dispensed from a selected pocket.

Preferably the operating means includes a common manually operable actuator member, movement of which operates both the operating means and piercing means for rupturing the seals.

Preferably, the operating means comprises a rotatable part of the housing which drives one of the coaxial tubes, preferably the outer tube.

The helically extending platform is preferably located between helical grooves in the facing surfaces of the inner and outer tubes and the pockets are indexed by rotation of one tube, preferably the outer tube, relatively to the other.

Preferably, only a single air passage is provided in the wall of each tube, so that these apertures have to be in alignment following each indexing actuation of the operating means. The operating means therefore preferably has an indexing stroke and a return stroke and a ratchet means is incorporated to enable the one tube, preferably the outer tube, to be rotated relative to the other tube without any pocket-indexing action during the return stroke.

Conveniently, therefore, in an embodiment, rotation of the one part of the housing in one sense rotates the outer tube, which in turn is caused by the ratchet means to index the pockets, whilst rotation of the one part of the container in the opposite sense rotates the outer tube reversely, but reverse indexing of the pockets is prevented by the ratchet means. In this embodiment, the inner tube is keyed against rotation to the fixed part of the housing.

The extent of rotation of the one part of the housing relative to the other, which determines the indexing and return strokes, is preferably limited by a stop means provided in combination on the inner and outer tubes. The length of the pocket indexing stroke corresponds to the spacing between the pockets of powdered medicament, which are preferably provided in immediate succession to one another around a helical path.

The mouthpiece preferably constitutes a fitting on the end of the fixed part of the housing, and may be provided with a removable cap. Conveniently, the air inlet is also provided on this fitting. Preferably, therefore, the airway used for sucking a dose of medicament into the mouth extends from the air inlet through the interior of the inner tube and back to the mouthpiece on the outside of the outer tube within the container.

Preferably, the inner and outer tubes and the pocket defining means between them constitute a replacement cartridge for the device, which device may conveniently be termed an inhaler. For this purpose, the rotatable part of the container preferably constitutes a removable cover which when fitted rotationally locks to the outer tube to enable indexing. However, when the cover is roved, a spent cartridge may be extracted and replaced by a fresh one.

According to another aspect of the invention therefore, there is provided a replacement cartridge for an inhaler which comprises inner and outer coaxial tubes which are relatively rotatable and between them support a helically extending platform defining a helically extending space partitioned to form pockets each containing a prescribed dose of self-supporting compressed powdered medicament, apertures in the walls of the tubes for aligning with the pockets and means for coupling one of the tubes to an external rotational drive provided by the inhaler in which the cartridge is to be inserted.

The apertures in the walls of the tubes may be initially sealed by removable or peel-off tabs. These tabs are then removed immediately prior to fitting the cartridge in the inhaler.

In accordance with previous description, when fitted into the inhaler, the inner tube preferably keys against rotation to the fixed part of the container while the subsequently fitted rotatable cover rotationally locks to the outer tube.

DESCRIPTION OF EMBODIMENTS

Two embodiments of an inhaler incorporating a replaceable cartridge carrying doses of powdered medicament and in accordance with the invention are now described, by way of example, with reference to the accompanying drawings, in which:

FIGS. 4–7 are exploded isometric views of various components of the cartridge of the second embodiment;

FIGS. 11A–11F are sectional plan views illustrating the operation of other parts of the second embodiment at corresponding stages in the operating cycle thereof;

FIG. 16 is a diagrammatic sectional side view of one example of apparatus for filling the containers shown in FIGS. 14 and 15, in the course of one stage of the method; and FIG. 17 shows the apparatus of FIG. 14 when being used to seal one side of the container, in accordance with a subsequent method step.

DETAILED DESCRIPTION

Figure 1A:
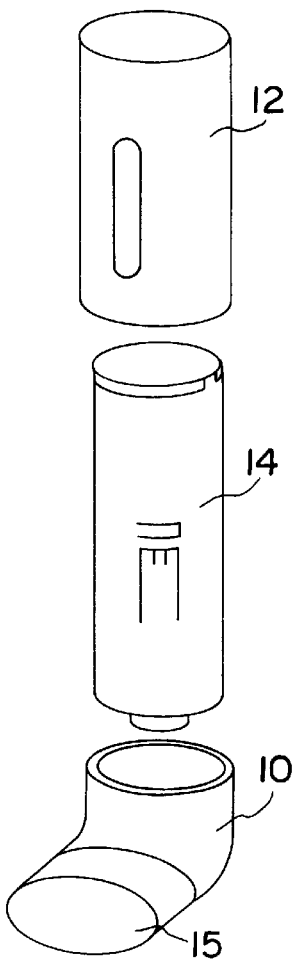
FIG. 1A shows the first embodiment in exploded view.

Referring to the drawings, and first to FIG. 1A in particular, the inhaler comprises a mouthpiece fitting 10, a cover 12 which when fitted is rotatable relative to the fitting 10, and a medicament-carrying cartridge 14 which is accommodated in the complete housing produced by the fitting 10 with fitted cover 12. Removable cap 15 is provided for the mouthpiece.

Figure 1B:
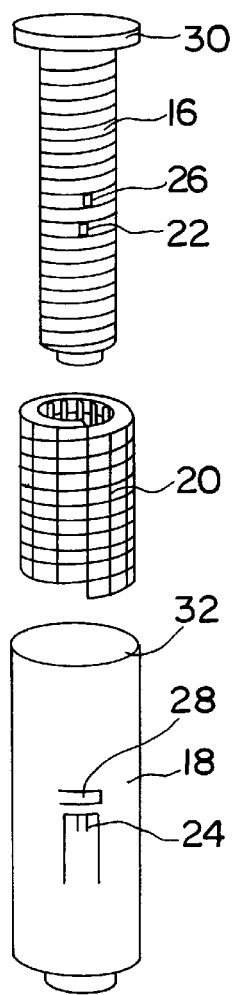
FIG. 1B shows the replaceable cartridge for the first embodiment.

The component parts of the cartridge 14, which is disposable when spent, are shown in FIG. 1B. This cartridge comprises an inner tube 16, an outer tube 18, and between them an element 20 which comprises a helically-extending platform defining a helically-extending space partitioned to form a succession of cavities which each contain in self-supporting manner a prescribed dose of powdered medicament. The platform is a helically-extending strip slidably seated in helical grooves in the facing surfaces of the inner and outer tubes.

Inner tube 16 has an aperture 22 for passage of air in its cylindrical wall, and outer tube 18 has an aperture 24 for passage of air. Additionally the tubes carry two angled tangs, a tang 26 on the inner tube 16 and a tang 28 on the outer tube 18. The tangs 26 and 28 are operable to engage the partitions between the cavities so as to provide a ratchet action mechanism by means of which relative rotational motion of the tubes 16 and 18 rotates the cartridge 14 in one sense only. Relative rotation of the two tubes is limited to a back and forth relative movement determined by stop means 30, 32 provided at the upper ends of the two tubes.

Figure 1C:
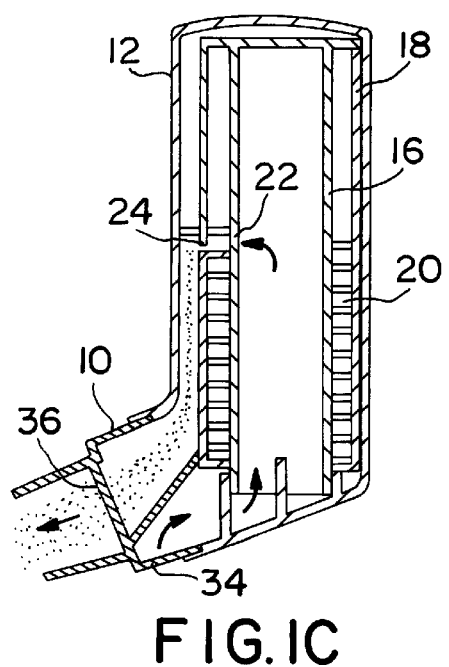
FIG. 1C shows the first embodiment of inhaler diagrammatically in cross-section.
Figure 2:
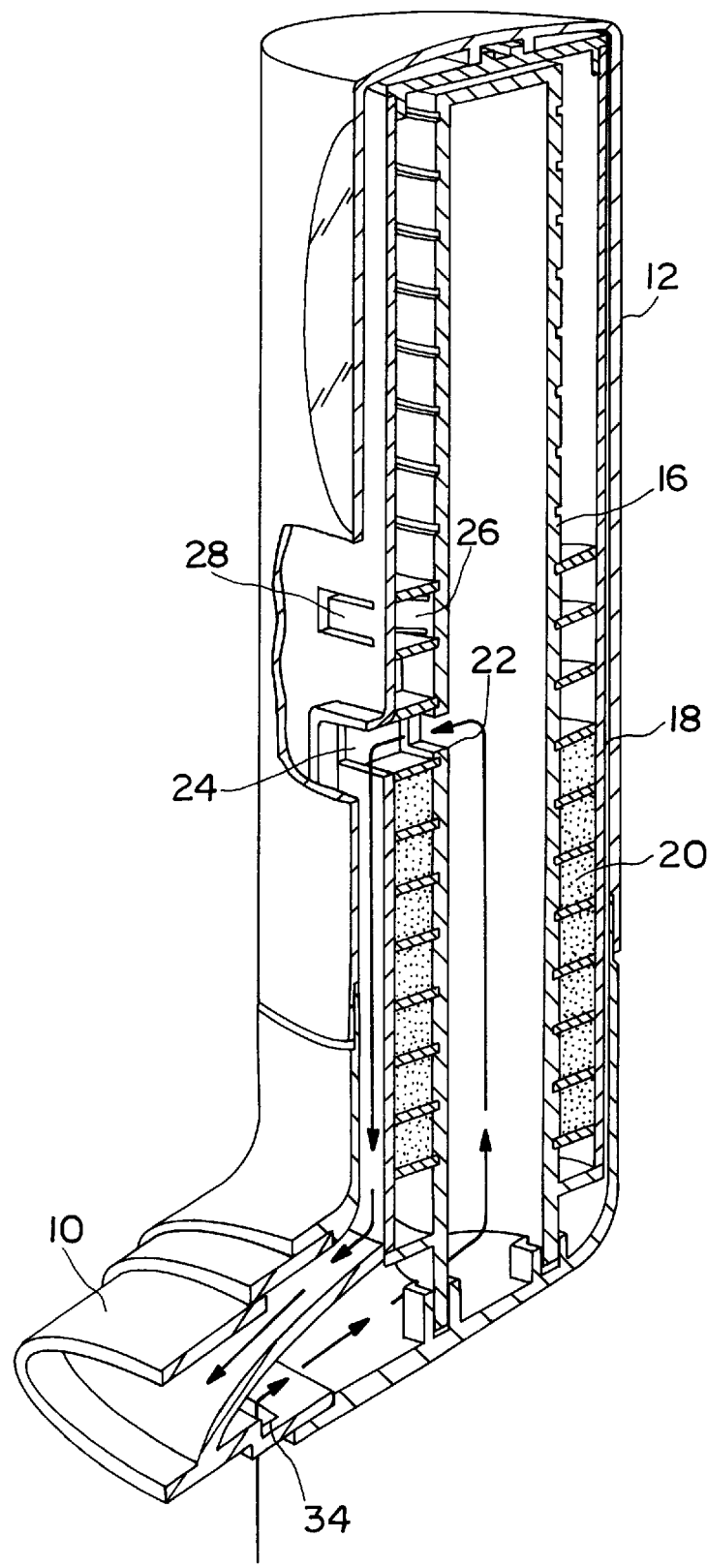
FIG. 2 is a more detailed view of the first embodiment of inhaler in cutaway cross-section.

FIGS. 1C and 2 show the interior of the complete inhaler, when assembled with a dose-carrying cartridge inside.

The mouthpiece fitting has an air inlet 34, partitioned from the mouthpiece exit, so that within the device there exists an airway, indicated by the marked arrows, extending from the air inlet 34 up through the inner tube 16 to the aperture 22, through a dose-containing cavity and the aperture 24 and down to the exit of the mouthpiece 10 on the outside of the outer tube 18. Thus, in use, a person requiring a dose of medicament can suck on the mouthpiece and draw the powdered medicament into the mouth entrained in the rush of air produced by the sucking action. Reference 36 denotes a grill provided in the mouthpiece fitting 10.

In order to receive a dose of medicament, the user must first index the inhaler so that an unused dose-containing cavity is brought into line with the airway. This is achieved by a rotational back and forth movement of the cover 12, which when fitted rotationally locks to the outer tube 18 (the inner tube 16 being rotationally keyed to the mouthpiece fitting 10 when the cartridge is inserted). When the outer tube 18 is rotated in one sense, ratchet tang 28 brings a fresh dose-containing cavity into position by engagement with the dose-carrying element 20, whilst when the outer tube is reversely rotated to bring the aperture 24 back into line with aperture 22, ratchet tang 26 prevents reverse rotation of the dose-carrying element. It will be noted that element 20 is axially shorter than the tubes, so that it can elevate through the inhaler as doses of medicament are used.

While the invention has been exemplified with reference to an inhaler capable of receiving a replacement cartridge, the invention is also concerned with a disposable inhaler wherein the assembly of inner and outer tubes and helical dose-carrying element between them are built-in during manufacture. The cover then simply constitutes a rotatable part of a closed non-openable housing.

Figure 3:
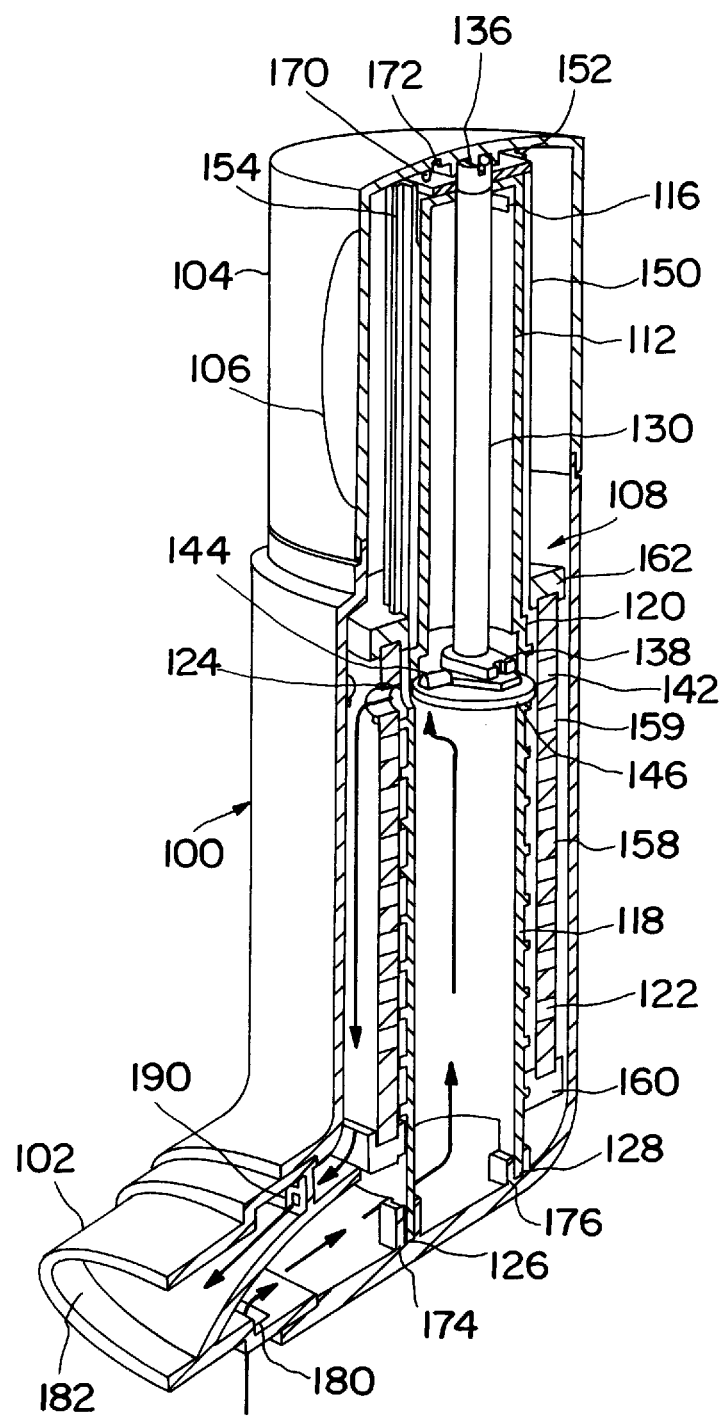
FIG. 3 is a partially cut away isometric view of a second embodiment of inhaler, having a cartridge assembly (which includes a cylindrical container) mounted within a housing.

With reference to FIG. 3, the inhaler in accordance with the second embodiment comprises a housing 100 which has a generally cylindrical main body and which is connected at its lower end to a mouth piece 102 extending substantially radially to the main body of the housing 100. The opposite end of the housing 100 includes a rotary member in the form of a cap 104 rotatably mounted on the rest of the housing 100. The cap 104 incorporates a window 106 through which a cartridge 108 contained within the body 100 can be viewed.

With reference to FIGS. 4 to 7, the cartridge 108 comprises a hollow cylindrical core 110 which has a reduced diameter upper portion 112 in which there is provided an upper aperture 114 and an integral tang 116. The core 110 also includes a lower portion 118 which is of a larger diameter than the portion 112, and which defines an annular shoulder 120 where it meets the portion 112. The portion 118 includes an external screw thread 122, a radial aperture 124 in its upper region, and two axially extending lower lugs 126 and 128.

The core 110 accommodates a vertical shaft 130, the upper part of which protrudes through the aperture 114. The top of the shaft 130 includes a slot 132 for engaging a protuberance 136 on the underside of the top of the cap 104 so as to provide a rotational key between the shaft 130 and the cap 104. The bottom of the shaft 130 is provided with a radial crank arm 138 which incorporates a radial slot 140 which slidably engages a boss 142 connected to a pin 144 positioned above a plate 146. The pin is in registry with an aperture (not shown) in the core 110 angularly spaced from the aperture 124.

The plate 146 is, with the cartridge assembled, attached to the interior of the core by suitable means (not shown), and the pin 144 and plate 146 include guide means (not shown) so arranged that rotation of the shaft 130 causes axial motion of the pin 144. With reference to FIG. 3, the shoulder 120 supports a sleeve 150 which is rotatably mounted on the core 110 and which surrounds the upper part 112.

The sleeve 150 includes internal longitudinal serrations 152 and two diametrically opposed sets of external longitudinal ribs 154 and 156.

With reference to FIG. 6, the medicament to be dispensed is contained in a cylindrical container 158 which has side walls which include a number of helically arranged radial through bores such as 159 (FIGS. 3 and 11), each of which contains a respective dose of material. The internal and external surfaces of the side walls are coated with corresponding sheets of a laminated foil which seal both ends of each bore.

The core 110 extends through the center of the container 158 which includes a lower end cap 160 having a part helical groove (not shown) for engaging the thread 122, and an upper cap 162 which includes two diametrically opposed sets of slots 164 and 166 which engage the sets of ribs 154 and 156 to provide a rotational key between the sleeve 150 and the container 158.

The upper portion of the shaft 130 includes a shoulder 133 which supports a ratchet member 168 which is rotatable with respect to the shaft 130. The ratchet member 168 includes an upper boss 170 which engages in an arcuate track 172 (FIG. 9) in the underside of the cap 104 to provide a lost motion connection between the cap 104 and the ratchet member 168.

Figure 8:
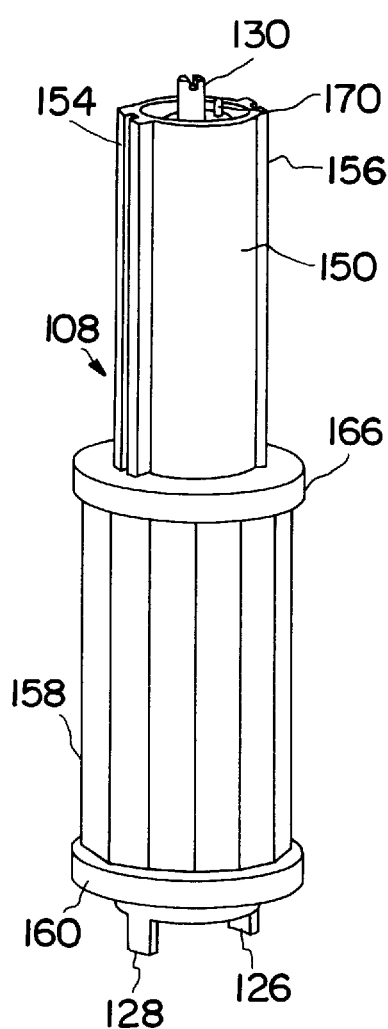
FIG. 8 shows that cartridge when assembled.
Figure 9:
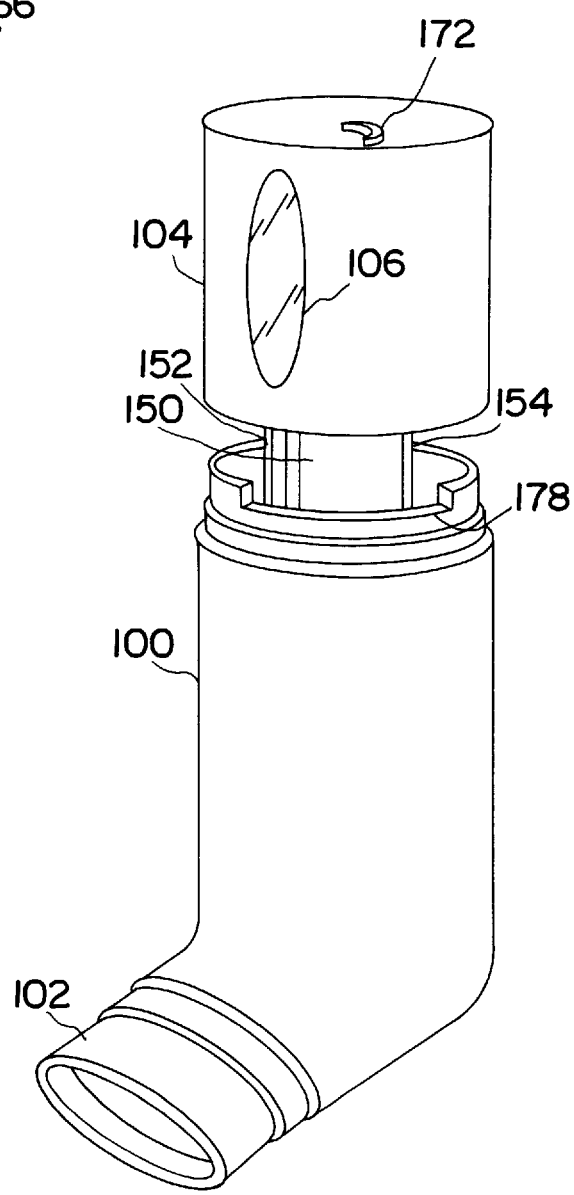
FIG. 9 is a diagrammatic partially exploded view of the cartridge and the housing of the second embodiment.

As is illustrated in FIG. 9, the cap 104 is removable from the rest of the housing 100 to enable the assembled cartridge 108 (as shown in FIG. 8) to be inserted into the housing 100 until the lower lugs 126 and 128 of the core 110 engage in corresponding sockets 174, 176 (FIG. 3) in the bottom of the housing 100 to provide a rotational key between the core 110 and the housing 100.

As is illustrated in FIG. 9, the housing 100 includes an upper rebate 178 which cooperates with a downwardly projecting lug (not shown) in the cap 104 to provide stops which define the limits of allowable rotational movement of the cap 104 relative to the rest of the housing 100.

The lugs 126 and 128 space the lower end of the core 110 from the housing 100, thereby enabling the interior of the core 110 to communicate with an air inlet 180 provided in the underside of the mouthpiece 102, which includes an air outlet 182 partitioned from the inlet 180. The container 158 is spaced from the housing 100 which includes vertical inner ribs 182 and 184 (FIG. 11) for defining a passage leading to the outlet 182.

Thus the inhaler includes an airway, indicated by the marked arrows, extending from the air inlet 180 up through the core 110, through the aperture 124 and a dose containing through-bore in registry therewith and then through the outlet passage down to the outlet 182. In order to take a dose of medicament from the inhaler, the user must rotate the cap 104 from one to the other of its end positions and back again, causing the pin 144 to rupture the foil seal for a through bore and causing the through bore subsequently to be moved into registry with the outlet passage. This operation will now be described in greater detail with reference to FIGS. 10A–10F, and FIGS. 11A–11F.

Figure 10A:
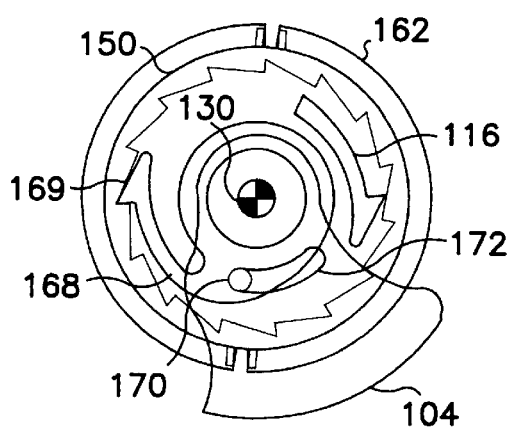
FIGS. 10A–10F are diagrammatic sectional plan views illustrating the operating of part of the second embodiment of inhaler at various stages during cycle of operation of the inhaler.
Figure 10B:
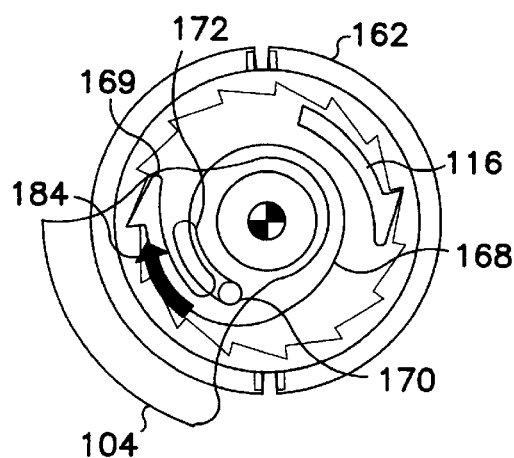
Figure 10C:
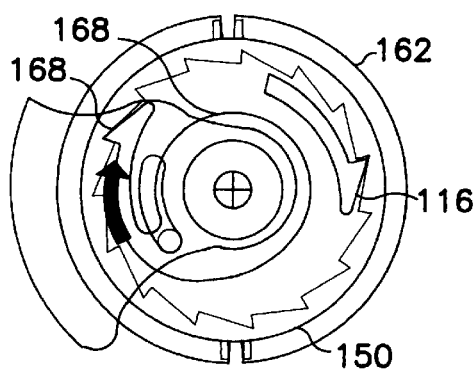

FIG. 11A shows the dispenser in an initial condition in which the pin 144 is retracted and all the compartments are sealed. Rotation of the knob 104 in a clockwise direction as indicated by the arrow 184 of FIG. 10B causes a corresponding rotation of the shaft 130 which, in turn, rotates the crank arm 138 so as to extend the pin 144 until it penetrates the inner seal of a cavity 186 (FIG. 10B). During this process, the slot 172 travels relative to the pin 170 so as to prevent rotation of the ratchet member 168 until the pin 170 engages the trailing end of the slot 172. Further rotation of the knob 104 in the same direction then also causes a corresponding rotation of the member 168 which can rotate relative to the sleeve 150 in a clockwise direction only. As this happens, the engagement of the tang 116 with the serrated inner edge of the sleeve 150 prevents the latter from rotating in an anticlockwise direction. When the limit of allowable clockwise rotation is reached, the member 168 is in the position shown in FIG. 10C and the pin 144 is in the position shown in FIG. 11C in which it extends through and beyond the bore 186 so as to pierce both inner and outer seals.

Figure 10D:
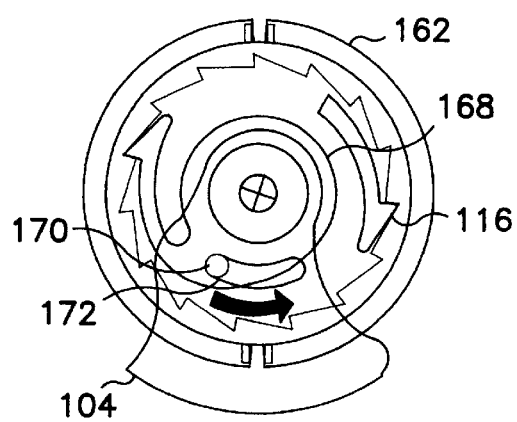
Figure 10E:
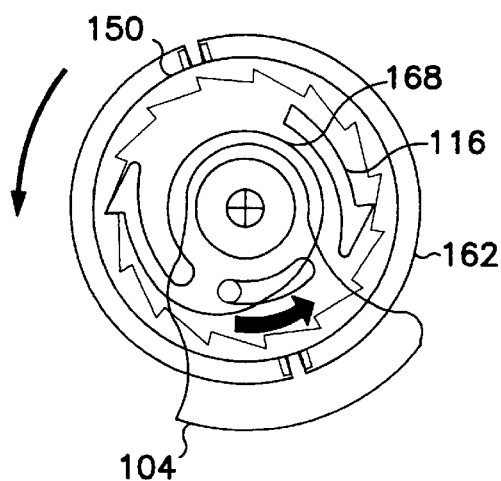
Figure 10F:
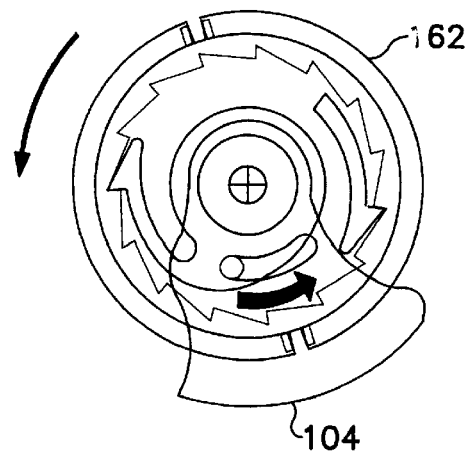

The knob 104 is then rotated in the opposite direction as shown in FIG. 10D, causing the pin 144 to be withdrawn from the bore 186. During the withdrawal of the pin 144, the slot 172 moves relative to the boss 170 so as to prevent corresponding movement of the sleeve 150 (and hence the container 158) until the pin 144 has been fully withdrawn. Further anticlockwise rotation of the knob 104 rotates the member 168, through the engagement of the boss 117 slot 172, in turn causing rotation of the sleeve 150. Since the latter is rotationally keyed to the container 158, this movement causes the container 158 to rotate on the lower portion 118 of the core 110, which in turn moves the through bores including the bore 186 along a part helical path as a result of the engagement of the cap 160 with the screw thread 122. By the time the knob 104 has reached the limit of allowable anticlockwise rotation, as illustrated in FIG. 10F, the bore 186 is in registry with the outlet passage (FIG. 11F).

If the user then inhales through the outlet 182 of the mouthpiece 102, the consequent airflow through the device expels medicament from the bore 186, into the outlet chamber and out through the outlet 182.

With reference to FIG. 3, the mouthpiece 102 also includes a grill 190 for capturing any loose fragments of the sealing foil which come adrift during inhalation.

Figure 12:
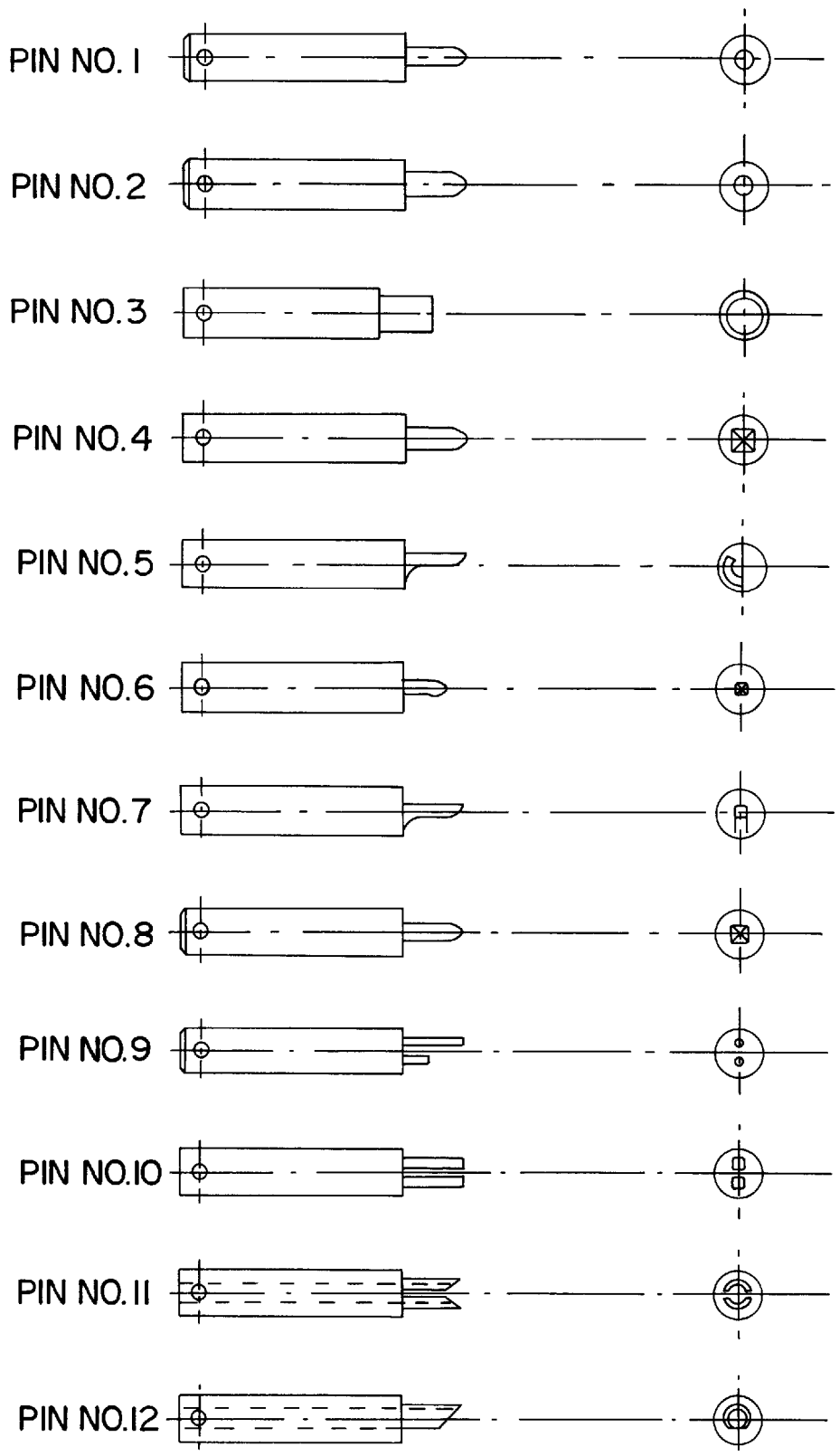
FIGS. 12 and 13 show a number of different versions of one of the components of the cartridge of the second embodiment.
Figure 13:
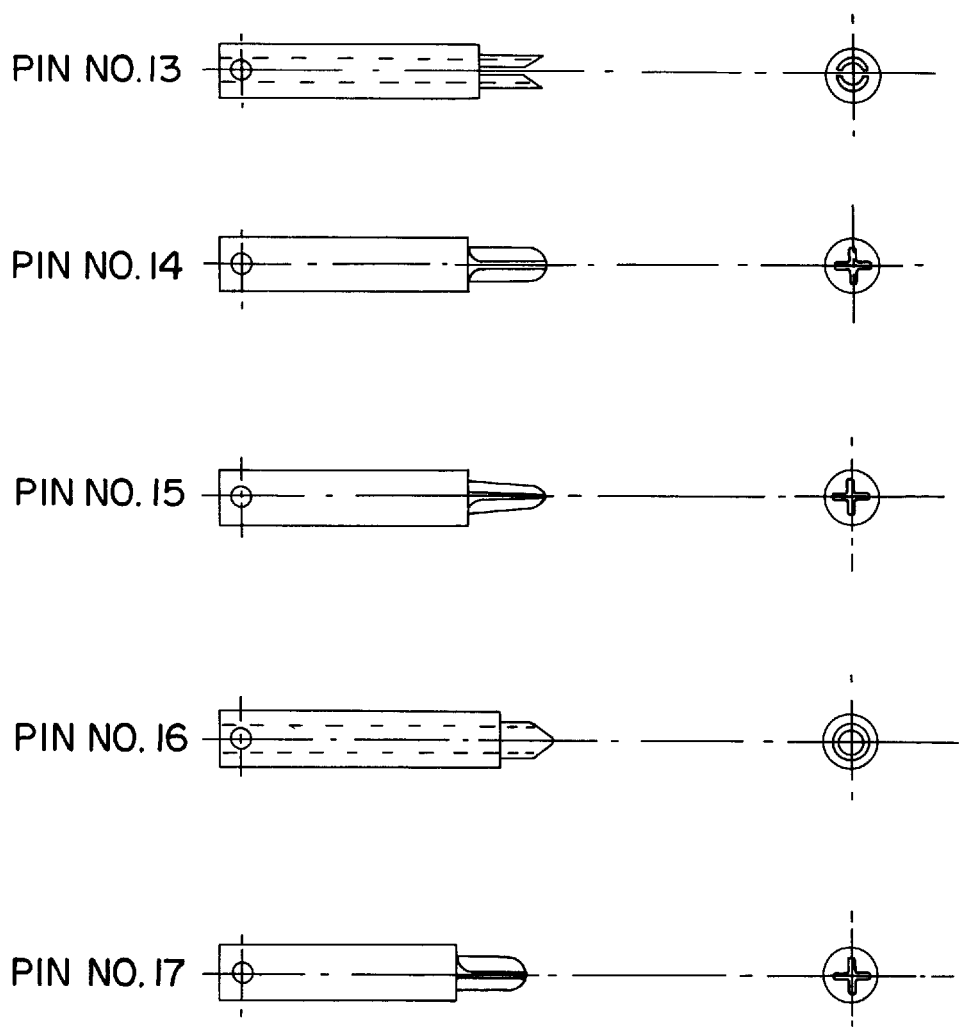

The pin 144 is of the kind shown as pin No 1 in FIG. 12. Pins Nos 2 to 17 shown in FIGS. 12 and 13 are alternative types of piercing members which can be used instead of pin No 1.

It will be seen that some of those members (eg Nos 5–11) have forward cutting edges (on right hand side of side views) so shaped to create flaps in the foil seals whilst minimizing the amount of material ejected from compartments during insertion. Those flaps are able to move, to allow material to be discharged, but are connected to the rest of the foil so as to reduce the chances of foil fragments breaking free during inhalation.

The danger of a user inadvertently taking an overdose by operating the cap a number of times before inhaling is avoided since material is only ejected into the outlet passage when the user inhales, and only from the bore in registry with the passage.

An example of one way in which the container 158 can be made is described below.

With reference to FIGS. 14A–H, the container comprises a body 201 which includes a number of through-bores, for example 202, for containing a respective dose of medicament. For the sake of clarity, the body illustrated in FIGS. 14A–H has only 16 such through-bores, although in practice a larger number of through bores may be present in the body 201.

With the container assembled, the body 201 is of a generally cylindrical shape, the bores being radially disposed, and the through bores are sealed by an outer sheet 204 and an inner sheet 206 of laminated foil attached to the body 201.

Figure 14A:
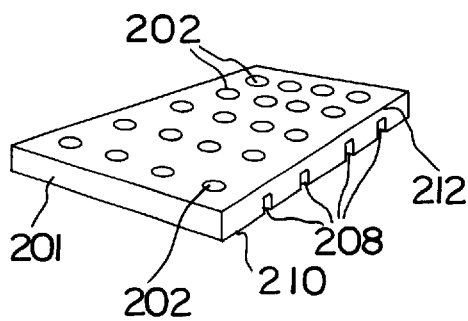
FIGS. 14A–14H are simplified diagrams showing various stages of an example of a method of making a tubular container for the second embodiment of inhaler.

With reference to FIG. 14A, the body 201 is formed from a rectangular plate, also referenced 201, of a plastics material, the underside of which includes a number of grooves 208 arranged in a regular parallel array. The grooves 208 divide the plate 201 into a number of parallel rigid strips, such as strip 210 running across the width of the plate, adjacent pairs of which are connected by corresponding reduced thickness portions, such as portion 212. The thickness of the plastics material constituting those portions is such that the adjacent strips are hingable adjacent to each other. The through bores in the body 201 are all provided in the strips.

Figure 14B:
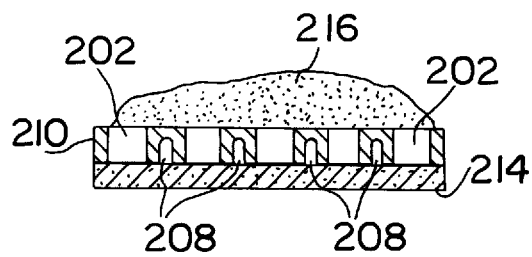

Turning to FIG. 14B, the plate 201 is placed on a bed 214 of a porous material, with the non grooved face of the plate upper most, and the upper surface of the plate 201 is covered with a layer of powdered medicament 216, which covers one end of each of the through bores in the plate 201.

Figure 14C:
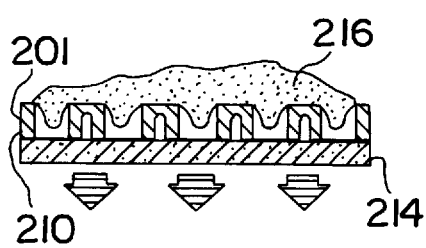
Figure 14D:
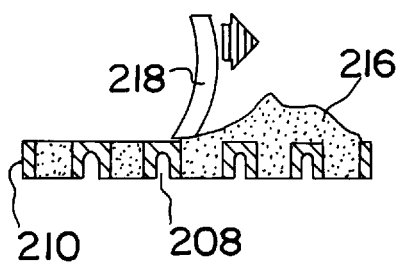
Figure 14E:
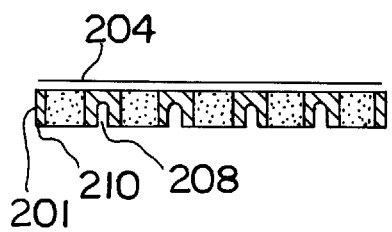

With reference to FIG. 14C, pressurized air is used to propel the material 216 into each of the through bores during which step air exits the bores through the bed 214. The porosity of the bed 214 is such that it is impervious to the material 216. As a result, the bed 214 prevents material 216 being discharged from the through bores to the lower end thereof.

Figure 14F:
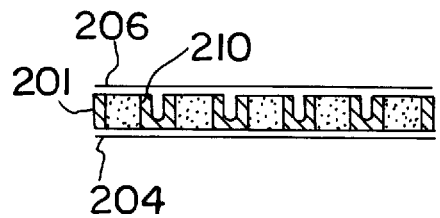
Figure 14G:
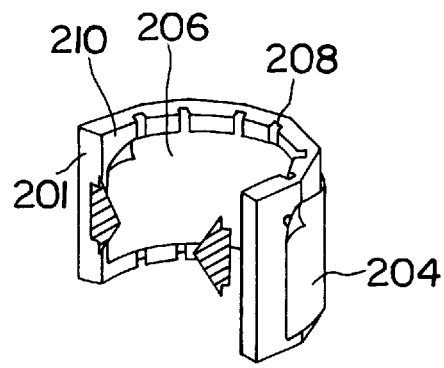
Figure 14H:
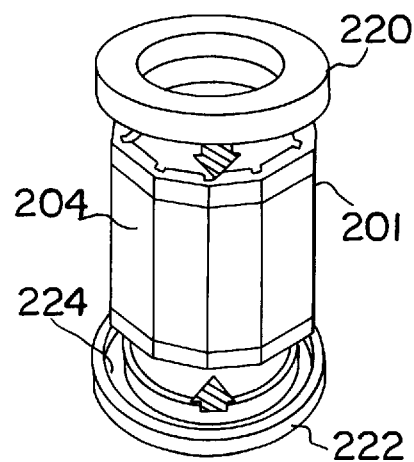

When the through bores have been filled with the material 216, any excess material which has not passed into a through bore is removed by drawing a resiliently flexible blade 218 across the upper surface of the plate 201 (FIG. 1D). The sheet 204 is then heat sealed onto the upper surface of the plate 201 (FIG. 14E), which is then inverted so that the sheet 206 can be similarly applied to the opposite face of the plate 201 (FIG. 14F).

The flexibility provided by the reduced thickness portions between the strips of the plate 201 enable the latter to be rolled (FIG. 14G) into a generally cylindrical shape, with the strips extending axially along the cylinder, and the grooves 208 on the inner surface thereof.

Once the body 201 has been formed by said rolling, two ring-shaped end caps 220 and 222 are applied one at each end of the cylinder. Each cap includes an annular track, such as track 224, into which the strips extend and in which the strips are a tight fit. Thus the caps 220 and 222 prevent the cylinder formed by the body 201 from unravelling. The components shown in FIGS. 15A–15E correspond with those shown in FIGS. 14A–H, and corresponding components are indicated by the same reference number raised by 30. Thus the container comprises a cylindrical body 231 formed from a plate, also referenced 231, having a number of through-bores, for example 232, which are filled with powdered medicament by means of the same method as illustrated in FIG. 14, and are then sealed on one side by a first sheet of laminated foil 234 and on the other side by a second sheet of laminated foil 236 applied to the plate 231 after the latter has been inverted.

The body 231 contains a larger number of through-bores, for example 232, than the body 201, and can therefore contain a greater number of doses of medicament than the body 201. In addition each of the grooves in the plate 231, for example groove 238, is tapered so as to facilitate the rolling of the body 231 into its cylindrical shape. The caps 250 and 252 each include diametrically opposed inner slot arrangements, for example 256 and 258 which enable the container to be rotationally keyed to the rotational core or an inhaler in which the container is to be used.

Figure 15A:
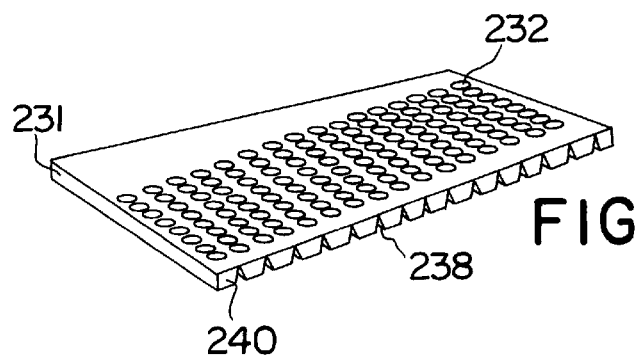
FIGS. 15A–15E show components of an alternative type of tubular container which can be filled by the method illustrated in FIGS. 14A–F, FIG. 15E showing the container when assembled.
Figure 15B:
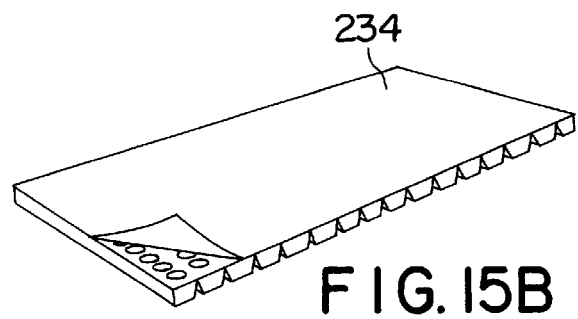
Figure 15C:
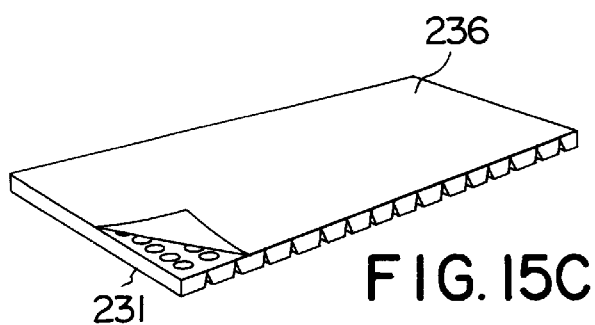
Figure 15D:
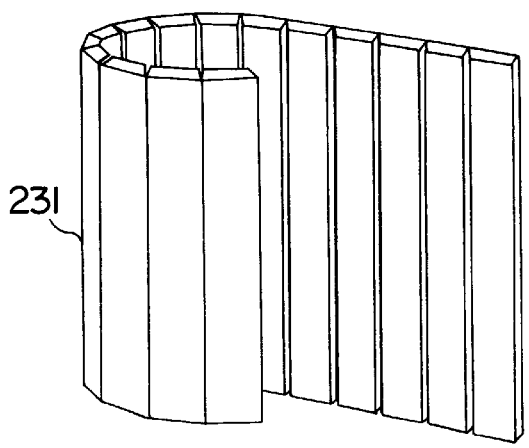
Figure 15E:
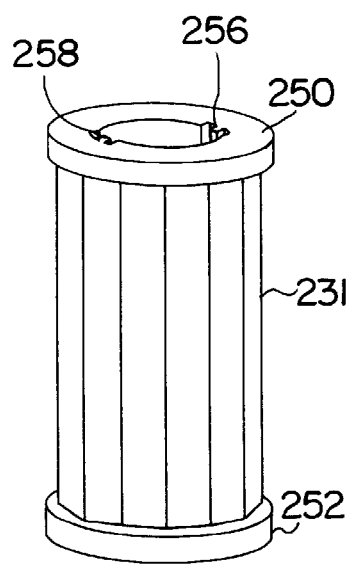

As can be seen from FIG. 15A, the through-bores are so arranged as to lie on a helical path on the body 231, when the container is assembled.

With reference to FIG. 16, apparatus for filling the container includes a filling station at which there is provided a filling head 260 comprising a rectangular upper plate 262 of corresponding dimension to the plate 264 to constitute a cylindrical body. Vertical peripheral walls 266 extend from the plate 262 to the plate 264 so that the head 260 and plate 264 define a filling chamber 268. The plate 262 includes a central aperture 270 which communicates with a air inlet 272. The chamber 268 contains a diffuser 274 positioned between the aperture 270 and the plate 264. The head includes a further inlet (not shown) through which the powdered material is introduced into the chamber 268 between the diffuser 274 and the plate 264.

In use, air is introduced into the chamber 268 through the aperture 270, fluidizing the powdered material in the chamber 268 and increasing the air pressure in the chamber. The increase in air pressure causes air to flow out of the chamber through the through-bores in the plate 264 and through a porous bed 216 on which the plate 264 is supported.

This flow of air draws material into the through-bores, thereby filling the latter.

The diffuser 274 ensures an even flow of air over the powder bed, so as to avoid any tendency for the incoming air to blow a hole in the powder. The diffuser 274 and bed 276 are of a similar porous material.

As is shown in FIG. 17, the head 260 is then moved laterally away from the plate 264, and a sheet of foil sealing material 280 is positioned over the body 264 by foil supply means (not shown) an upper heater block 282 is also moved into registry with the plate 264 and is then lowered vertically onto the foil 280 and plate 264 so as to seal the foil 280 onto the plate.

The apparatus includes means (not shown) for inverting the plate 264 to enable a sheet of foil to be applied to the opposite side in the same way, and means (not shown) for rolling the plate into a cylindrical form.

We claim:

1. A device for dispensing single doses of a particulate material, the device comprising a housing carrying a mouthpiece which communicates with an air inlet through an airway within the housing, a cylindrical container contained within the housing, the container having a plurality of compartments therein, each compartment containing a respective dose of particulate material, operating means for moving the container relative to the airway so as to bring successive compartments into registry with the airway and enable the doses of medicament to be discharged therefrom, wherein the compartments are angularly and axially spaced relative to each other so as to define a helical path which is substantially coaxial with the axis of the container.

2. A device according to claim 1, in which part of the airway extends along an axial passage within the container.

3. A device according to claim 2, in which said part of the airway extends along at least part of the elongate axis of the container.

4. A device according to claim 1, in which the container comprises a cylindrical body having a plurality of radial bores, each of which constitutes a respective compartment.

5. A device according to claim 1, in which the container comprises inner and outer respectively rotatable coaxial tubes within the housing, a helically extending platform between the tubes defining a helically extending space, said space being partitioned to define said compartments lying on a helical path and each containing a discrete dose of a powdered medicament, and apertures for passage of air in the walls of the inner and outer tubes, said apertures lying in the path of the airway.

6. A device according to claim 1, in which the device includes sealing means for retaining the doses of material in the corresponding compartments.

7. A device according to claim 6, in which the sealing means comprises one or more membranes covering the compartments, the device including means for rupturing each membrane to allow the powdered material to be dispensed from a selected compartment.

8. A device according to claim 7, in which the operating means includes a common manually operable actuator member, movement of which operates both the operating means and the means for rupturing the membranes.

9. A device according to claim 7, in which the actuator member comprises a rotatable part of the housing.

10. A device according to claim 8, in which the actuator member has an indexing stroke and a return stroke and in which a ratchet action means is incorporated to enable the actuator to be rotated relative to the container without any indexing action during the return stroke.

11. A device according to claim 9, in which the extent of allowable rotation of the one part of the housing relative to the other is limited by a stop means.

12. A device according to claim 10, in which the length of the indexing stroke corresponds to the spacing between the compartments of powdered medicament, the compartments being arranged in immediate succession to one another around said helical path.

13. A device according to claim 9, in which the mouthpiece constitutes a fitting on the end of the fixed part of the housing.

14. A device according to claim 13, in which the air inlet is also provided on this fitting.

15. A device according to claim 9, in which the container constitutes a replacement cartridge for the device, the rotatable part of the housing constituting a removable cover which, when fitted, rotationally locates on to the cartridge to enable indexing, but which, when removed enables a spent cartridge to be removed and replaced by a fresh cartridge.

16. A replacement cartridge for an inhaler which inhaler comprises a device according to claim 1, the cartridge comprising a cylindrical container having a plurality of separate compartments, each containing a prescribed dose of powdered medicament, arranged in a helical path, and means for coupling the container to an external rotational drive provided by the inhaler in which the cartridge is to be inserted.

* * * * *